United States Patent [19]

Pelanek

[11] Patent Number: 5,132,085
[45] Date of Patent: Jul. 21, 1992

[54] TEST DEVICE WITH NOVEL CONTROL SYMBOLISM

[75] Inventor: Geraldine A. Pelanek, Webster, N.Y.

[73] Assignee: Eastman Kodak Company, Rochester, N.Y.

[21] Appl. No.: 663,239

[22] Filed: Feb. 28, 1991

Related U.S. Application Data

[63] Continuation-in-part of Ser. No. 533,443, May 11, 1990, abandoned.

[51] Int. Cl.$^5$ .................. G01N 33/53; G01N 33/543; G01N 33/545; C12M 1/12
[52] U.S. Cl. .................................. 422/55; 422/56; 422/57; 422/58; 422/59; 422/60; 422/61; 435/288; 435/293; 436/169; 436/809
[58] Field of Search ............... 436/169, 170, 178, 809; 435/293, 300, 311, 288; 422/55-60, 102, 104

[56] References Cited

U.S. PATENT DOCUMENTS

| | | | |
|---|---|---|---|
| 4,046,513 | 9/1977 | Johnson | 427/288 |
| 4,073,623 | 2/1978 | Bodart | 356/191 |
| 4,523,852 | 6/1985 | Bauer | 422/55 |
| 4,877,580 | 10/1989 | Aronowitz et al. | 422/58 |
| 4,916,056 | 4/1990 | Brown, III et al. | 435/7 |
| 4,920,046 | 4/1990 | McFarland et al. | 435/7 |
| 4,923,800 | 5/1990 | Ly | 435/10 |
| 4,943,522 | 7/1990 | Eisinger et al. | 435/7 |

FOREIGN PATENT DOCUMENTS

| | | |
|---|---|---|
| 217403 | 10/1986 | European Pat. Off. . |
| 249418 | 6/1987 | European Pat. Off. . |
| 264036 | 10/1987 | European Pat. Off. . |
| 335244 | 3/1989 | European Pat. Off. . |
| 90/09596 | 2/1990 | PCT Int'l Appl. . |

*Primary Examiner*—David L. Lacey
*Assistant Examiner*—William Chan
*Attorney, Agent, or Firm*—Dana M. Schmidt

[57] ABSTRACT

There are described assay devices having a control surface on which controls are deposited to produce a representational symbol that preferably indicates a satisfactory test procedure, or a failure in the test procedure. In one aspect of the invention, the symbol comprises exclusively the positive control areas and the negative control area, so that the negative control area will convert the "satisfactory" symbolism into "unsatisfactory" symbolism. In another aspect, the symbols that are formed are "OK" and "OK", respectively.

19 Claims, 4 Drawing Sheets

FIG. 5
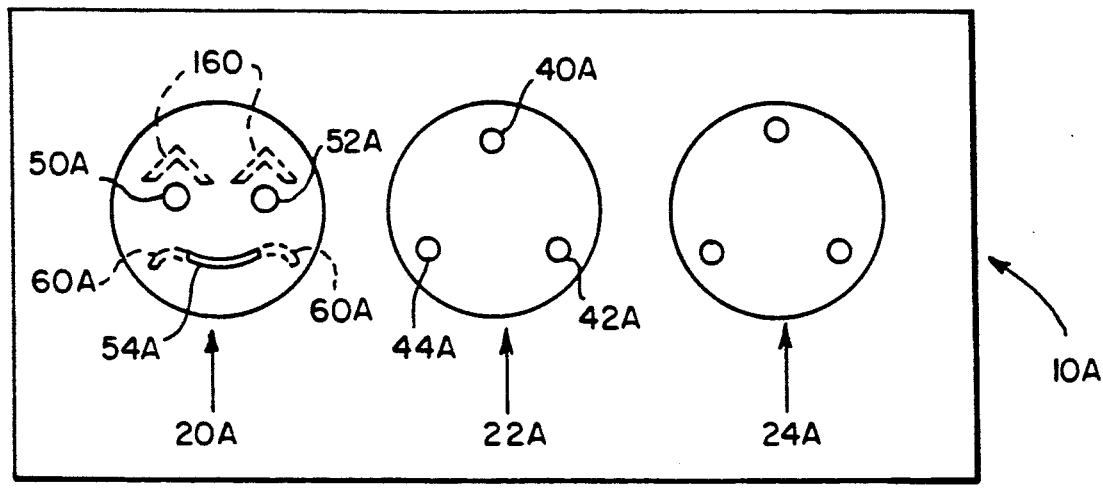
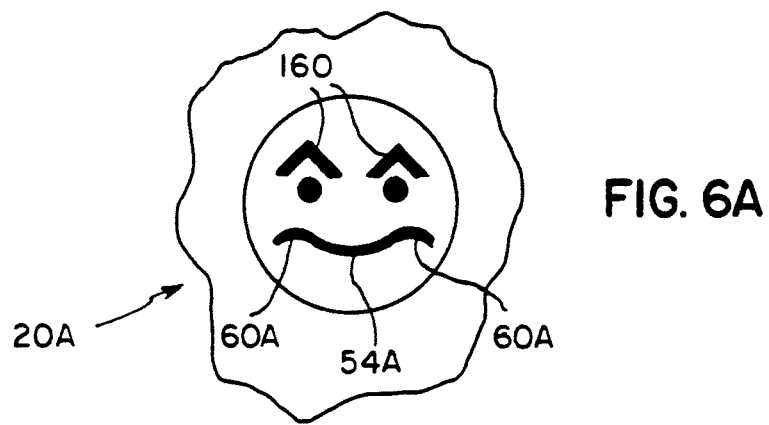
FIG. 6A
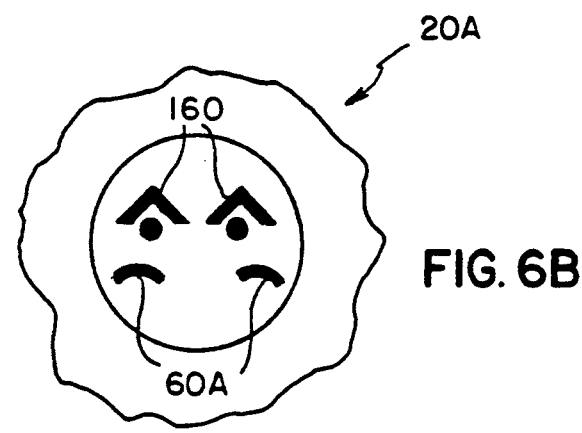
FIG. 6B

1

TEST DEVICE WITH NOVEL CONTROL SYMBOLISM

This is a continuation-in-part of application Ser. No. 533,443, filed May 11, 1990, now abandoned.

FIELD OF THE INVENTION

The invention relates to an assay device used to detect patient conditions such as infectious diseases, and the controls that indicate a satisfactory device and a satisfactory procedure were used. More specifically, it relates to the construction of the control areas to produce symbols upon signal development.

BACKGROUND OF THE INVENTION

In the field of simplified test kits based upon immunoassays, for example, pregnancy tests and tests for infectious diseases, it is conventional to run a positive control and a negative control as well as the patient sample.

The point of the positive control is to produce a detectable indication, for example a color change, that will always occur if the reagents are functioning properly. That is, the positive control indicates the device is functioning in a way such that, if the test antigen were present in the patient sample, there would also be a similar detectable indication produced. On the other hand, the point of the negative control is that occasionally, some error or interferent will be introduced such that, even in the presence of the target antigen, the test is defective even though the positive control may produce a visual indication suggesting (erroneously) that all is well.

In the early stages of development of these devices, the positive and negative controls were simple color changes over a target area. A problem with such devices is that a simple color change can be confusing—does the change in color of a particular dot mean the test is OK, or does it mean it is not OK? Partially in response to this need, the test devices have become more sophisticated. One type, for example those described in EPA Publication Nos. 217,403; 264,036; 249,418 and 335,244, causes the positive control area to produce a color change in conjunction with the patient sample area to give a combined symbol that represents either a "negative" condition or a "positive" condition. Not surprisingly, the symbols produced are "−" and "+", respectively. This achieved by having the positive control always form the horizontal cross-bar, which without an antigen in the patient sample, produces a "minus" sign. However, any targeted patient antigen present causes the vertical bar to also develop color, converting the "−" into a "+".

Such a "+" and "−" system may be satisfactory when testing for a single antigen, but it is not particularly useful in combination tests, such as periodontal assays, that test for more than 1 antigen at once. Such a combination of tests needs a positive control for each antigen being tested, and a corresponding symbol representation for that separate positive control. Furthermore, the conventional "+" and "−" system requires the negative control, which it not used with the "+" or "−", to form some unrelated symbol somewhere else, if the test fails, for example, because the antibodies have denatured. aforesaid EPA 217,403 and its U.S. counterpart U.S. Pat. No. 4,916,056 do not even produce a representational symbol, for an invalid test. Instead, if the test is invalid, NO specific, predetermined and connected signal is produced whatsoever (as shown in FIGS. 3A, 4A, 6A and 7A in the '056 patent.) This is unsatisfactory, as such a result leaves a question in the user's mind as to what actually happened.

Therefore, there has been a need prior to this invention for an immunoassay test device that causes positive controls for multiple antigens to combine together to form a meaningful symbolic indication whether the test is performing satisfactorily or not, for all the antigens. There has been a further need to combine the negative and positive controls into one general location to produce a symbolic representation that covers all aspects of the device's satisfactory performance, and not just the positive control's satisfactory performance.

SUMMARY OF THE INVENTION

I have constructed an assay device that solves the above noted problems.

More specifically, in accord with one aspect of the invention there is provided a solid phase assay device for use in a binding assay to determine the presence of an analyte in a liquid sample, the device comprising a reaction surface having at least one positive control area, a negative control area and a patient sample-analyte area, at least two of the areas taken from any two of the positive control, the negative control and the patient sample-analyte being combined and configured together so that the two areas produce, in the presence of an appropriate analyte, a representational symbol informative of the test result. The device is improved in that the two areas configured together are the positive and negative controls on the reaction surface, and the symbol is indicative of either of two exclusive alternatives: that the test device and procedure are operating satisfactorily, or they are not operating satisfactorily.

In accord with another aspect of the invention, there is provided a solid phase assay device for use in a binding assay to determine the presence of an analyte in a liquid sample, the device comprising a reaction surface having at least one positive control area, a negative control area and a patient sample-analyte area, at least one of the areas being configured to produce, in the presence of an appropriate analyte, a symbol representing the actual results of the test. The device is improved in that the at least one area is configured to produce the representational symbol "OK".

Accordingly, it is an advantageous feature of the invention that an assay device is provided for simultaneously assaying multiple antigens with a positive control for each antigen producing part of a symbolic representation of whether the assay is performing satisfactorily, the symbolic representation being complete only if all positive controls are indicative of success.

It is a further advantageous feature that such a device combines both the negative and the positive control areas into one combined symbolic representation, avoiding the user having to check a plurality of locations.

It is a related advantageous feature of the invention that the above-noted combined symbolic representation is understood in more than one language.

Other advantageous features will become apparent upon reference to the following Description of the Preferred Embodiments, when read in light light of the attached drawings.

BRIEF DESCRIPTION OF THE DRAWINGS

FIG. 5 is a plan view similar to that of FIG. 1, but of an alternative embodiment of the invention;

FIGS. 6A and 6B are fragmentary plan views of the embodiment of FIG. 5, similar to that of FIG. 4A, illustrating the result when the negative control indicates a failure.

DESCRIPTION OF THE PREFERRED EMBODIMENTS

The invention is described in connection with certain preferred embodiments, in which the reaction surface is described as part of a solid phase device having a certain physical structure and operation, to test for multiple periodontal antigens using a preferred conjugate. Also, the disclosure is one in which the symbolism is used for the control areas only. In addition, the invention is useful regardless of the physical structure used with the reaction surface, regardless of the number and type of antigens being detected, and regardless of the chemistry or the type of conjugate used. Furthermore, the invention is useful for multiple antigen tests to provide a representational symbol in the patient sample area as well—the "OK" portion can be formed as the positive control area and the negating "slash" bar can be formed from the patient sample area, so that label that attaches because the target antigen is present in the patient sample, produces a "NOT OK" symbol, meaning the patient is "not OK".

As used herein, "solid phase assay" refers to an immunoassay wherein antibodies are bound to a solid phase, such as a polymeric bead, so that unwanted soluble materials can be removed by washing and/or filtration.

Figure 1:
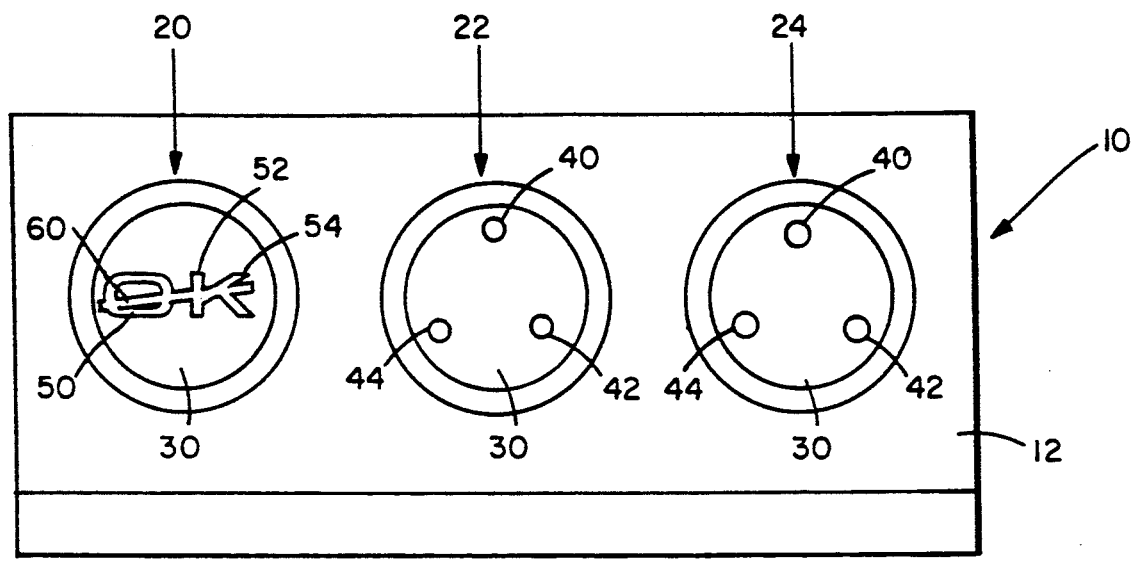
FIG. 1 is a plan view of a device constructed in accordance with the invention, and particularly of the test wells of the device.

As shown in FIG. 1, device 10 of the invention preferably comprises a frame 12 having three recesses or wells 20, 22 and 24 at the bottom of which is a reaction surface 30 comprising an appropriate membrane, this membrane in turn being in contact with a liquid-absorbing material (not shown) underneath. The entire construction of device 10 in its physical manifestations apart from surface 30, is not part of this invention. Rather, such structure, the preferred forms of surface 30, and the operation of device 10 are described in commonly-owned U.S. application Ser. No. 240,179 filed on Sep. 6, 1988 by Hinckley et al, now U.S. Pat. No. 494,677, the details of which are hereby expressly incorporated by reference.

Reaction surface 30 has applied thereto beads to which have been chemically attached, antibodies that are selective to an appropriate antigen. Any kind of beads and chemical bonding of the antibody can be used. Most preferred, however, are the beads described in commonly-owned U.S. Ser. No. 081,206 filed Aug. 3, 1987, now abandoned and refiled as continuation-in-part co-pending application Ser. No. 315,086 on Feb. 24, 1989 entitled "Avidin- And Biotin-Immobilized Reagents, Analytical Elements and Method of Use". Methods of attaching antibodies to those beads are also described in these references. The antibodies are preferably polyclonal, but monoclonal can also be used.

Beads

As described particularly in the aforesaid Ser. No. 081,206, the beads are generally water-insoluble latex particles having a particle size greater than about 0.01 micrometers, preferably in the range of from about 0.01 to about 5 micrometers, and more preferably from about 0.3 to about 3 micrometers.

Particularly useful beads include those described in EP-A-0 323 692 (published Jul. 12, 1989). These are generally water-insoluble latex particles having an average particle size greater than about 0.01 micrometers. They are composed of polymers prepared from one or more ethylenically unsaturated polymerizable monomers at least one of which has active halo atoms, activated 2-substituted ethylsulfonyl or vinylsulfonyl groups. Monomers having reactive carboxy groups are also very useful.

One or more of the monomers described above can be polymerized individually or in combination to form homo- or copolymers. Alternatively, and preferably, one or more of them are copolymerized with at least one other ethylenically unsaturated polymerizable monomer. Generally such monomers provide various desirable properties such as hydrophobicity, dispersibility or other features. Particularly useful comonomers are described in EP-A-0 323 (noted above).

Representative useful polymers include the following: poly(m & p-chloromethylstyrene), poly(styrene-co-m & p-chloromethylstyrene-co-2-hydroxyethyl acrylate) (67:30:3 molar ratio), poly[styrene-co-m- & p-(2-chloroethylsulfonylmethyl)-styrene] (96:4 molar ratio), poly{styrene-co-N-[m & p-(2-chloroethylsulfonylmethyl)phenyl]acrylamide} (99.3:0.7 molar ratio), poly(m & p-chloromethylstyrene-co-methyacrylic acid) 95:5, 98:2 and 99.8:0.2 molar ratio), poly[styrene-co-m & p-(2-chloroethylsulfonylmethyl)styrene-co-methacrylic acid] (93.5:4.5:2 molar ratio), poly{styrene-co-N-[m & p-(2-chloroethyl sulfonylmethyl)phenyl]acrylamide-co-methyacrylic acid} (97.3:0.7:2 molar ratio), and poly(styrene-co-m & p-chloromethylstyrene)(70:30 molar ratio). Poly[styrene-co-m & p-(2-chloroethylsulfonylmethyl)styrene], (96:4 molar ratio) is preferred.

Further details relating to these polymers and representative materials can be found in U.S. Pat. Nos. 4,161,407 and 4,548,870 noted above.

Such beads are immobilized on the exterior of surface 30 in each of the wells in the following patterns:

In wells 22 and 24, the areas that are deposited are exclusively for patient sample, either two runs of the same sample (for replication) or for 2 different patients or different patient sites. Each of the wells have three head deposits 40, 42 and 44. Deposit 40 has antibodies specific for the periodontal antigen derived from *Actinobacillus actinomycetemcomitans* (hereinafter Aa), deposit 42 for the antigen derived from Bacteroides (*Porphyromonas*) *gingivalis* (hereinafter Bg) and deposit 44 for the antigen *Bacteroides intermedius* (hereinafter Bi).

Figure 2:
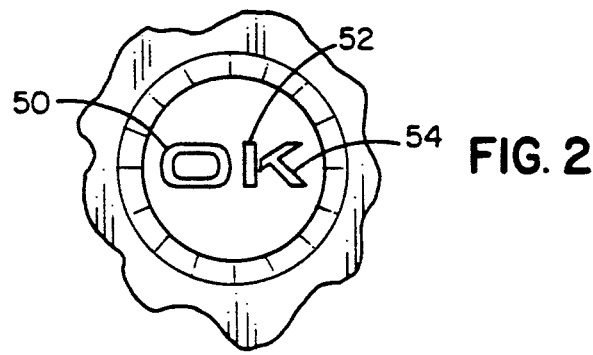
FIG. 2 is a fragmentary plan view of only the control well of FIG. 1, with the negative control area not shown for clarity.

Well 20, on the other hand, has bead deposits that are exclusively for controls, both negative and positive. Deposit area 50 comprises beads with antibodies specific to the Bi antigen, deposit area 52, FIG. 2, comprises beads with antibodies specific to the Aa antigen, and deposit area 54 comprises beads with antibodies specific to the Bg antigen. In addition, each of these three antibodies is already complexed, as manufactured, with the noted antigen—Aa in the case of area 50, Bi in the case of area 52, and Bg in the case of area 54, FIGS. 1 and 2. This insures that, if a viable labeled conjugate reagent is properly added as part of the procedure, the positive control areas will all form a detectable symbol.

Still further, and in accord with one aspect of the invention, well 20 also includes deposit area 60 formed in combination with areas 50, 52 and 54, FIG. 1. The shape of area 60 produces a symbol that is the negative of the symbol produced by areas 50, 52 and 54. For example, as shown, area 60 is a diagonal bar or slash, having the universally recognized meaning of, "not" or "negative". It is area 60 in which there is deposited beads having thereon some non-specific antibody. For example, in the case of periodontal assays, an antibody non-specific gamma globulin from rabbits is useful, provided it binds to nothing of interest. The species used is the same as the species of polyclonals used in the sample test, e.g., rabbit.

As will be apparent from the precedinng, the area deposited by each of the positive control beads is broken up so that any one type specific for one of the test antigens (Aa, Bi or Bg), forms only part of the total symbol used, and together they form the entire symbol. In accord with another aspect of the invention, the representational symbol formed is "OK", one that is universally recognized. Any break-up of that symbol among the three antigens is useful—as shown area 50 forms the "O", area 52 forms the vertical left portion of the "K" and area 54 forms the right portion of the "K". Similarly, other symbols can be used, and indeed they need not be recognizable in more than one language, but such more generalized recognizability is obviously preferred.

Still further, it is not critical in what order the wells appear. Thus, well 20 can just as well be switched with either well 22 or 24. Also, the number of patient sample wells 22 and 24 that is present in unimportant—it can be as few as 1 and as maany as desired.

Anitbody Preparation

The procedure described in commonly owned copending U.S. application Ser. No. 468,393, filed on Jan. 22, 1990 by H. S. Reynolds et al, entitled "Bacteroides Polyclonal Antibodies and a Method for Their Preparation" is preferred. In this procedure, an immunizing amount of a sample of cells of a predetermined serotype of a Bacteroides microorganism is injected into a suitable mammal host using standard injection techniques. Alternatively, a component of the cells can be injected as long as that component includes at least one necessary antigenic site (such as cell surface carbohydrates or cell proteins) which will generate the production of the desired antibodies from an immune reaction. Such cellular components may be different for various serotypes. These are identified herein as "antibody-producing" components of the microorganism.

Representative useful mammalian hosts include horses, sheep, goats, rabbits, rodents and others known to one skilled in the art. Rabbits are preferred for convenience, cost and specificity of response to injections. New Zealand white rabbits are most preferred. The injection can be introduced into a suitable body part of the mammal (for example, the nape of the neck or hind pad of a rabbit) or supplied intravenously.

What constitutes an "immunizing amount" will depend upon the particular mammalian host used in the invention, and the particular Bacteroides serotype of interest. Generally, this amount can be characterized as at least about $1.25 \times 10^4$ cells of the appropriate microorganism (or an equivalent amount of an antibody-producing component thereof) per gram of host mammal weight. More usually, the immunizing amount will be from about $1.5 \times 10^5$ to about $4 \times 10^6$ cells of the appropriate microorganism (or an equivalent amount of an antibody-producing portion thereof) per gram of mammal weight.

For example, for the preferred rabbits noted above, a suitable immunizing amount is from about $2.5 \times 10^4$ to about $3.75 \times 10^6$ cells (or an equivalent amount of anitbody-producing component per gram of rabbit weight. This can be expressed in another manner, namely for rabbits averaging about 4000 grams in weight, the injection would generally contain from about 0.5 to about 1.5 ml of a sample of a suspension of the microorgamism (or antibody-producing component thereof), which sample contains from about $10^7$ to about $10^{10}$ whole cells (viable or nonviable) per ml. Thus, for any host, the sample size of the injection will depend upon the mammal weight and the concentration of microorganism cells (or weight) per ml of injected fluid. For the preferred rabbits noted above, a preferred injection comprises from about 0.5 to about 1 ml having from about $10^8$ to about $10^9$ cells per ml.

Whole live cells are obtainable from any number of public sources (such as repositories) or isolates from patient samples which have been plated or broth cultured, harvested and optionally, washed with a suitable buffer prior to injection. In one instance, the cells are anaerobically cultured on agar plates as opposed to culturing in broth. The cells can be stored in buffer at low temperatures prior to use if desired. Representative examples of available serotypes of *Bacteroides intermedius* (B.i.) and *Bacteroides(Porphyromonas) gingivalis* (B.g.) are identified as follows:

| Serotype | Source |
| --- | --- |
| B.i. serotype A | ATCC 25611 |
| B.i. serotype B | NCTC 9336 |
| B.i. serotype C | ATCC 49046 |
| B.g. serotype A | ATCC 33277 |
| B.g. serotype B | ATCC 53978 |
| B.g. serotype C | ATCC 53977 |

ATCC refers to the American Type Culture Collection (Rockville, Md.) and NCTC refers to the National Collection of Type Cultures (London). Other *Bacteroides intermedius* serotypes are identified in the Nakazawa et al reference noted above. Other *Bacteroides(Porphyromonas) gingivalis* serotypes are identified in U.S. Pat. No. 4,661,350 (issued Apr. 28, 1987 to Tsurumizu et al) and U.S. Pat. No. 4,458,014 (issued Jul. 3, 1984 to Ebersole), both incorporated herein by reference.

The predetermined serotype cells or antibody-producing components thereof injected into the mammal are usually provided in an aqueous buffered suspension. The suspension can be frozen until used. Any suitable buffer can be used to provide a pH of from about 6 to about 9. Representative buffers include phosphate buffered saline solution, tris(hydroxymethyl)aminomethane, tricine, bicine, N-tris(hydroxymethyl)methyl-2-aminoethanesulfonic acid and others known in the art.

Following the first injection, and between the second and fifteenth days after that injection, the mammal is immunized at least one time with a boosting amount of a certain serotype or antibody-producing component thereof. Preferably, at least two such injections are given in this time period. These additional injections are often called "booster" injections in the art. The term "boosting amount" is defined herein similarly to "immunizing amount", that is the amount of cells or antibody-producing components thereof is based on the weight of the host mammal. A boosting amount can be the same as or different than the initial immunizing amount, but preferably, it is at least twice as much as the immunizing amount used in the first step of the method. One having skill in the art would readily know how much the booster injection should contain for a given mammal and initial injection amount. Generally, each boosting injection has from about $1.5 \times 10^5$ to about $3.5 \times 10^6$ bacterial cells (or an equivalent amount of an anitbody-producing component thereof) per gram of mammal weight. The amount in each booster injection can be the same or different.

At any time after the initial injection, a sample (for example 1-2 ml) of mammal serum can be taken for determination of the antibody performance using known techniques, for example by immunofluorescence. Preferably, the antibody performance is determined using a disposable test device like that commercially available in Surecell ™ test kits from Eastman Kodak Company. This test device has a polyamide microporous membrane which can capture an immunological complex for detection. Thus, during such antibody tests, a test device having immobilized antigen can be used to capture anitbodies present in the serum sample. The complex can be detected using known procedures, such as reacting it with an anti-antibody which is labeled for detection.

More particularly, initial screening is carried out by directly binding antigen to a nylon microporous membrane, followed by complexing the bound antigen with pure IgG antibodies directed thereto from the antisera. Uncomplexed materials are washed through the membrane. This complex is detected by further immunological reaction with a peroxidase-labeled anti-antibody. Again, uncomplexed materials are washed through the membrane. Addition of hydrogen peroxide and a triarylimidazole leuco dye provides a visible dye in the presence of the enzyme on the membrane.

If the initial screening is positive, the antibodies from the antiserum are screened using a sandwich assay.

Beginning with the fifteenth day after the initial injection of the mammal, a booster injection is given to the mammal at least three times every seven-day period thereafter for at least four seven-day periods. The three booster injections can be spaced out over each seven-day period in any suitable fashion. Generally, they are given every other day. The concentrations in these injections are also based on the mammal weight, and are generally within the range noted above for the other booster injections. As noted above, each booster injection can be the same or different in concentration as previous or successive injections. Preferably, they are all the same, and the concentration is about twice that of the initial immunizing injection.

Preferably, the booster injections are carried out for at least ten seven-day periods, and most preferably for eleven seven-day periods after the fifteenth day.

Following the last booster injection, antisera containing the desired antibodies is removed from the mammal in a suitable manner. Where the mammal is sufficiently large, antisera can be removed without sacrificing it. Generally, however, where rabbits and other small mammals are used, they are usually sacrificed to obtain sufficient amounts of antisera.

The polyclonal antibodies prepared according to this procedure can be stored and supplied in a buffered solution (as noted above). Generally, the pH of this solution is from about 6 to about 9, and contains one or more suitable buffers as described above. Others would be readily apparent to one skilled in the art.

The following examples are intended to illustrate the antibody preparation.

PREPARATION 1

Preparation of Polyclonal Antibodies Directed to Sertypes of *Bacteroides intermedius* (Bi)

In this example, polyclonal antibodies to three serotypes of *Bacteroides intermedius* were prepared. These strains are referred to as serotype A (ATCC 25611) serotype B (NCTC 9336) and serotype C (ATCC 49046).

These bacterial strains were supplied as viable cultures by Homer S. Reynolds (SUNY, Buffalo, School and Dentistry). Isolates were anaerobically cultured on CDC anaerobic plates (BBL Laboratories, Baltimore, Md.) supplemented with hemin (5 µg/ml) and menadione (0.5 µg/ml).

The plates were then incubated for 24-48 hours at 37° C. in an anaerobic chamber. Frozen stocks were prepared for each strain by harvesting the colonies with an inoculating loop, preparing a cell suspension in skim milk and freezing the suspension at −70° C. Viability of the frozen stock was tested by plating a portion of the frozen stock onto CDC anaerobic plates and incubating as described above. Once viability was determined, fresh isolates for each strain could be obtained in a similar manner. Cell suspensions were prepared by harvesting colonies with an inoculating loop, placing the loop in phosphate buffered saline solution (pH 7.5, 1 ml) and vortexing vigorously for about one minute.

Concentrations of cell suspensions were determined spectrophotometrically by measuring turbidity at 620 nm. Appropriate dilutions were prepared to yield an optical density in the range of 0.1 to 1. Concentrations were determined using a 1 McFarland standard wherein $OD_{620}=0.180$, corresponds to about $3 \times 10^8$ cells/ml.

Ten New Zealand white rabbits were intravenously injected with 0.5 ml of a phosphate buffered saline solution (pH 7.3) solution of the respective immunogen containing about $5 \times 10^8$ whole viable cells per ml. The injections were given following the method shown in McCarty and Lancefield (*J.Exp.Med.*, 102, pp. 1-28, 1955).

Two booster injections were given as follows: one week after the initial injection, each rabbit was injected again with the same amount of immunogen, and one additional week later, each rabbit was similarly injected.

Beginning with the fifteenth day after the initial injection, for a total of eleven additional weeks, each rabbit was given a booster injection of 1 ml of immunogen ($5 \times 10^8$ cells/ml) three times per week. the booster injections were spaced out every other day over each seven day period. Samples (2 ml) of antisera (for each serotype) were collected from the rabbits at various times to determine the antibody performance at those times. For example, antisera samples were taken at three, six and nine week intervals after the initial injection of immunogen. The rabbits were then sacrificed at thirteen weeks after the initial injection and the antisera was collected (about 100 ml per rabbit).

The final sera were then purified using ammonium sulfate precipitation. Saturated ammonium sulfate solution was added dropwise with stirring to each serum sample, cooled on ice until 45% saturation was achieved. After the addition, the mixture was stirred for an additional ten minutes, centrifuged and the supernatant discarded. The pellet was resuspended in a volume of phosphate buffered saline solution (pH 7.3) equal to the amount of the original sample being purified. The noted steps (addition of ammonium sulfate, centrifugation and resuspension of the pellet) were repreated. The mixture was then transferred to dialysis bags and dialyzed for about fifteen hours to 4° C. with stirring against phosphate buffered saline solution (pH 7.3). About 200-10,000 times excess of dialysis buffer was used. The dialysis was repeated with fresh buffer for an additional six hours. The solutions were removed from the dialysis bags and filtered through a 0.22 $\mu$meter filter. A portion of the filtrate was diluted in the range of 1:10 to 1:100 in phosphate buffered saline solution, and the absorbance was read at 280 nm. The antibody concentration was determined according to the formula:

$A_{280} \div [1.4 \times (dilution)] =$ antibody conc. (mg/ml)
The antibody solutions were then diluted to 2-4 mg/ml with phosphate buffered saline solution (pH 7.3) and merthiolate (0.01 weight %) and stored at 4° C. (for small amounts whereas large amounts were stored at $-70°$ C.).

PREPARATION 2

Preparation of Polyclonal Antibodies Directed to Serotypes of *Bacteroides(Porphyromonas) gingivalis* (Bg)

This example is similar to Preparation 1 except that the polyclonal anitbodies are directed to *Bacteroides(Porphyromonas) gingivalis*. Polyclonal antibodies directed against two strains of *B. gingivalis* were prepared. These strains are referred to as serotype A (ATCC 33277) and serotype C (ATCC 53977).

These strains were supplied as viable cultures by Homer S. Reynolds (SUNY, Buffalo School of Dentistry). To prepare cell suspensions for immunization purposes, the isolates were cultured in anaerobically prepared brain heart infusion broth (Difco Laboratories), supplemented with hemin (5 $\mu$g/ml) and menadione (0.5 $\mu$g/ml) for 36 hours at 20°-25° C. The cells were washed twice with phosphate buffered saline solution (using a volume equivalent to the original volume of the solution) before inoculation. Cell suspensions were used in the determination of antibody performance as described in Preparation 1 above.

Antisera samples were taken at three, seven and ten and a half week intervals after the initial injection. The immunized rabbits were then sacrificed at sixteen and a half weeks after the initial injection, and the antisera was collected (about 100 ml per rabbit). The antisera was purified using ammonium sulfate precipitation as described in Preparation 1. Antibody performance was determined at the different bleed intervals and at sixteen and a half weeks using the sandwich assay procedure noted above.

Method of Application

Any convenient method of applying the antibody-carrying beads can be used. For example, injection metering or free-drop application can be used. A preferred method is the application under positive displacement of a solution of beads through a porous applicator that touches off the solution onto the reaction surface 30, the applicator having the desired shape of the desired pattern. For example, for area 50 of the "O", an oval-shaped annulus is used for the applicator. For the slash or bar 60, a rectangular, bar-shaped applicator is used. Preferably, the negative control beads are deposited first, and dried before overcoating.

The porosity of the contacting surface of the application is selected to readily pass the bead solution. For example, 40 micron pores are adequate. Preferably, the applicators are constructed of porous, high density polyethylene, for example, these obtainable under the trademark "Interflo" ® from Chromex Corp. As is conventional, "high density polyethylene" means polyethylene that is polymerized using a catalyst that minimizes branching and thus allows the polymer chains to pack closely together. A preferred catalyst for such materials is the Ziegler-Natta catalyst.

The following non-limiting example is illustrative:

An "O"-shaped applicator of the type described above, having 40 micron pores, is connected to a solution of beads bearing the positive control antibody-Bi antigen complex, at a concentration of from about 0.01% to about 2.0%, and most preferably 0.25% to 1.0%. The applicator is touched onto reaction surface 30 in the control well 20, and the desired volume is pumped through the applicator with a positive displacement applied to the solution to cause solution to transfer to surface 30. Enough time and volume are used to give a coverage of from about 2.8 mg/cm$^2$ to about 37 mg/cm$^2$, using a solution that is 0.95% solids. Most preferably, coverage is about 26 mg/cm$^2$. The dispensing can occur before or after initial contact.

Use

The test procedure using device 10 is a sandwich assay, in which the antibody on the beads complexes with its antigen (if present), which in turn complexes with a conugate antibody bearing an appropriate label, that is added later. Preferably, such a label is an enzyme, that reacts with a later-added substrate to produce a signal, preferably a color. If no antigen is present, the conjugate antibody washes through reaction surface 30 so as to leave no signal (color). The chemistry of this procedure is well-known so that the steps that are required need no further description.

Figure 3A:
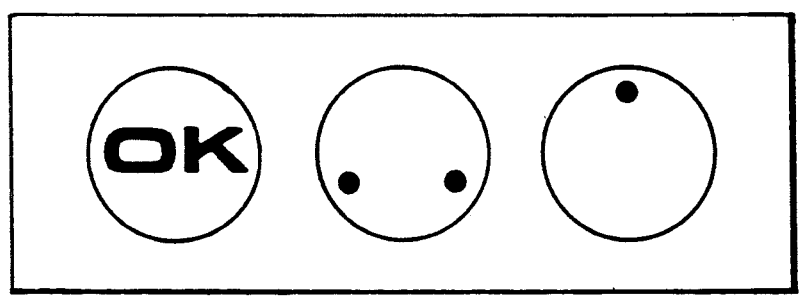
FIGS. 3A and 3B are plan views similar to that of FIG. 1, illustrating two of the possible visual symbols producable by the device that represent a satisfactorily operated device and procedure.
Figure 3B:
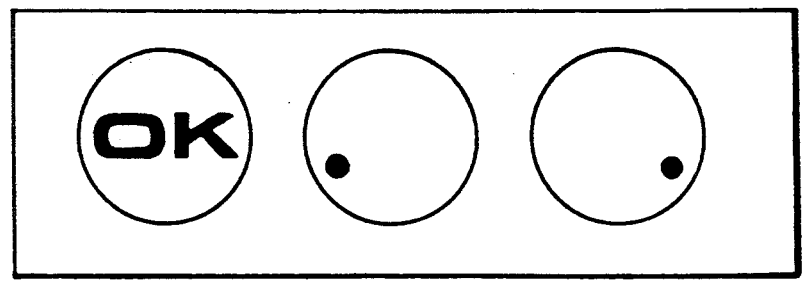

FIGS. 3A and 3B illustrate a successful test procedure using the controls and the assay device described above. That is, in both cases, well 20 produces the visually observable symbols "OK", since only the the positive controls function to produce a signal. Thus, the results in wells 22 and 24 are valid. In the case of FIG. 3A, patient sample in well 22 shows positive for Bi and Bg, whereas the patient sample in well 24 is positive only for Aa. In the case of FIG. 3B, well 22 shows positive for Bi, and well 24 shows positive for Bg.

Figure 4A:
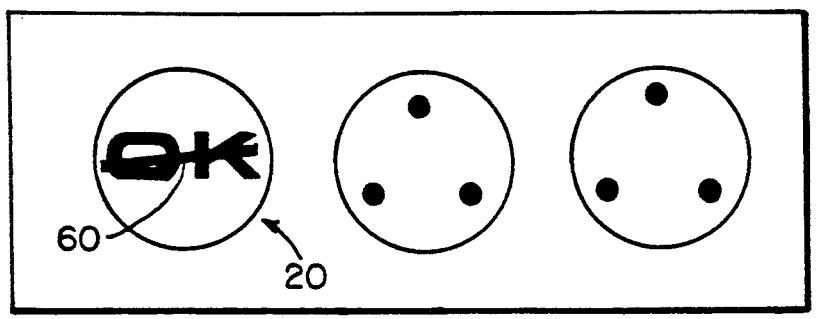
FIGS. 4A–4E are plan views similar to those of FIGS. 3A–3B, except that the visual symbols presented are some of those that are indicative that either the reagents or the procedure, or both, were unsatisfactory and the test is invalid.
Figure 4B:
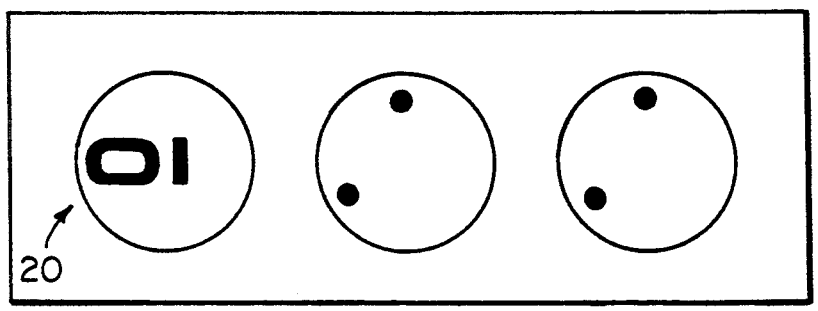
Figure 4C:
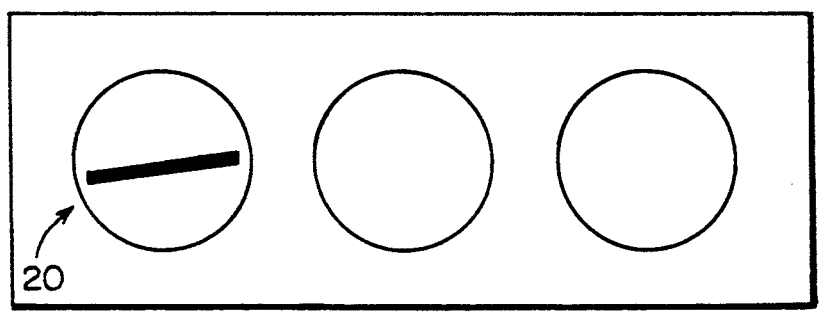
Figure 4D:
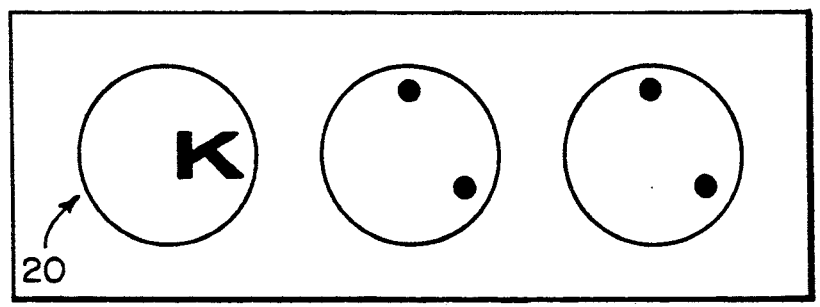
Figure 4E:
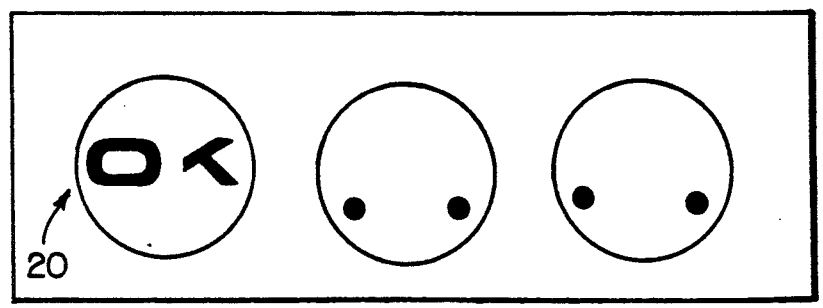

However, in FIGS. 4A-4E, all of the test results are invalid, as indicated by the control well 20. In FIG. 4A, although the "OK" forms a visual signal, the negative control also produces its symbol representation, indicating for example that the test reagents are defective. That is, bar 60 negates the "OK" representation. In FIGS. 4B, 4D and 4E, the negative control of well 20 does not produce its symbol, but the tests fail because one or more of the positive controls fail to print up to form a complete "OK". This indicates a failure on part of the conjugate or the antibody for one or more of the tests being run. Finally, in FIG. 4C, not only is there a complete failure of the positive controls, but also the negative control does print up, meaning a failure on the part of the antibodies to be specific, or some other catastrophic failure.

Alternatives

It should be readily apparent that the above-described embodiment will readily accommodate more than 3 different antigens in the combination test. If 4 are used, for example, the "O" area, area 50, can be divided into two parts formed by the control for antigen Bi and the control for the 4th antigen.

Other symbolic representations are also useful for the control well, particularly those having recognition in more than one language. FIGS. 5 and 6 illustrate one other such representation. Parts similar to those previously described bear the same reference numeral, to which the distinguishing suffix "A" is appended.

Thus, FIG. 5, device 10A features three wells 20A, 22A and 24A as before, with well 20A being the control well. Areas 40A, 42A and 44A of reaction surface 30A in each of the sample wells 22A and 24A have beaded antibodies to the antigens Aa, Bg and Bi, respectively, as before.

However, in well 20A, the areas of reaction surface 30A to which the controls are applied, are a different shape. Specifically, a facial expression is to be created during the test, and to this end, the control areas 50A and 52A are shaped to form the eyes of the face. Thus, they are dots, one of which is the positive control for Aa and the other for Bi or Bg, for example. Control area 54A, then, is the remaining control for Bg or Bi, and is shaped to form a smiling mouth. Thus, the positive control areas, shown in solid lines, FIG. 5 form a so-called "smiley face", which is known internationally to be equivalent to "OK". If the positive control areas print up visually during the test, as expected, the smiling face is indicative of a satisfactory test and satisfactory materials.

The negative control beads and antibodies are applied to areas 60A and 160. Areas 60A form downturned corners on the mouth of the face, and areas 160 form scowling eyebrows, so that, if they print up, FIG. 6, (as is not expected), they convert the smiling face into a frown that is a clear indication that the test has failed. FIG. 6B indicates that the negative control areas 60A and 160 are still effective to convey the "bad" impression, even if, e.g., control area 54A fails to print up.

Alternatively (not shown), wells 22, 24 or 22A, 24A can be shaped differently from well 20 or 20A, respectively, but identical to each other. Such shapes are a visual indication to the user that the patient sample wells are to be handled differently from the way in which the control well is handled.

Figure 7:
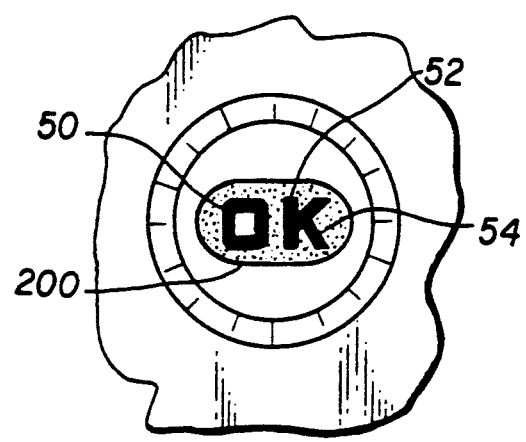
FIG. 7 is a plan view similar to FIG. 2, but of an alternate embodiment.

Yet another embodiment of the invention features the use of a negative control occupying an area of a dot 200 under but connected to and extending beyond the entire representational symbol area of the positive control, FIG. 7. The surface area occupied by the two controls is less than the total surface area of the reaction surface, as is clearly shown in FIGS. 1 and 7. This dot area uses chemistry such that if the test is invalid, the dot produces a predetermined representational color symbol uniform in appearance and connected to the positive control so as to give a positive indication that the test is invalid. (This is an improvement over assays that produce nothing if the test is invalid.)

More specifically, the negative control area can be formed by beads immobilized in that area to which antibodies specific to $A_a$, $B_i$ and $B_g$ are immobilized (in admixture). Because only labeled conjugates and washes go into the well with these controls, no color will normally form in this dot area. (The patient sample is added to a different well and therefore to a different reaction surface.) However, if the conjugate solution or wash solution is contaminated or invalidated by the presence of antigen for $A_a$, $B_i$ or $B_g$; or if the reagents have deteriorated so as to non-specifically bind to the capture beads in the absence of antigen, then dye color is produced at the dot area to create a uniform color connected to the symbol otherwise produced by only the positive control. Preferably, such color forms as a dot surrounding the positive control areas. Such a dye color is a positive indicator that the test has gone wrong.

The positive control area symbol, both in this embodiment and in the ones heretofore described, can also be varied by omitting from the solutions that are deposited to form those areas, the bead and antibody. Instead, only the antigens ($A_a$, $B_i$ and $B_g$) need to be deposited to form the desired symbol area, and dried. These are sufficient, when contacted with labeled conjugate, to form the visible symbol without washing through the reaction surface.

The invention has been described in detail with particular reference to preferred embodiments thereof, but it will be understood that variations and modifications can be effected within the spirit and scope of the invention.

What is claimed is:

1. In a solid phase assay device for use in a binding assay to determine the presence of an analyte in a liquid sample, the device comprising a plurality of reaction surfaces which comprise at least one of positive control area, a negative control area and a patient sample analyte area, wherein at least one of said reaction surfaces have at least two of said areas taken from any two of said positive control, said negative control and said patient sample analyte combined and configured together so that said two areas produce, in the presence of an appropriate analyte, a representational symbol selected from words and pictures that a) are of a predetermined, connected shape b) are informative of the test result and its validity, the improvement wherein said at least two areas configured together are the positive and negative controls on one of said reaction surfaces and said symbol is formed so as to be indicative of either of two exclusive alternatives: that the test device and procedure are operating satisfactorily, or they are not operating satisfactorily, and further wherein said patient sample analyte area is on another of said reaction surfaces and spaced away from said reaction surface of said two control areas, and wherein said two control areas occupy only the approximate center portion of the reaction surface containing them so that they occupy less than the total area of said reaction surface containing them, so that false positives are readily distinguished by the user.

2. An assay device as defined in claim 1, wherein said positive control area includes a separate subarea for testing for a plurality of antigens, said subareas being disposed and configured such that when all positive controls for all of the antigens react as expected to each produce part of the representational symbol indicative of satisfactory operation, then the indicative symbol will be complete.

3. An assay device as defined in claim 1 or 2, wherein said negative control area occupies the area of a diagonal slash that is connected to the representational symbol produced by said positive control area.

4. An assay device as defined in claim 3, wherein said representational symbol produced by said positive control area is the symbol "OK".

5. An assay device as defined in claim 3, wherein said representational symbol produced by said positive control area is the symbol "OK", each of said subareas contributing to a portion only of said "OK", so that the failure of any one positive control will prevent the complete formation of the symbol.

6. An assay device as defined in claims 1 or 2, wherein said areas occupied by said positive and negative controls form a facial expression having recognition in more than one language.

7. An assay device as defined in claim 6, wherein said positive control area is configured to produce the eyes and a smile of said facial expression.

8. An assay device as defined in claim 7, wherein said negative control area is configured to convert said smile into a frown, if the negative control area is active to signal a failure in the negative control.

9. An assay device as defined in claim 2, further including periodontal disease antigens.

10. An assay device as defined in claim 9, wherein said antigens comprise the periodontal antigens Aa, Bi and Bg, and said positive control area includes immobilized reagent for each of said periodontal antigens.

11. An assay device as defined in claim 1 or 2, wherein said areas each comprise immobilized binding reagent for a label, said binding reagent for a positive control area being active to bind a label regardless of the presence of the target analyte in the patient sample, said binding reagent for said sample-analyte binding area being effective to bind label only in the presence of said target antigen in the patient sample, and said binding agent in said negative control area being effective to form a visual signal if there is non-specific binding of reagents.

12. An assay device as defined in claim 1, wherein the area occupied by said negative control is such as to produce, in an invalid test, a representational symbol known to be a negation of the representational symbol produced by said area of the positive control.

13. An assay device as defined in claim 12, wherein the area of said negative control is a dot that is under and extends beyond said positive control area, and comprises chemistry that produces a visible dye build-up if the test is invalid.

14. An assay device as defined in claim 12 wherein said negative control area and the resulting representational symbol of negative is one having recognition in more than one language.

15. In a solid phase assay device for use in a binding assay to determine the presence of multiple analytes in a liquid sample, the device comprising a plurality of reaction surfaces which comprise at least one of positive control area, a negative control area and a patient sample-analyte area, at least one of said areas being configured to produce, in the presence of an appropriate analyte, a predetermined connected symbol representing the results of the test;

the improvement wherein said at least one area is configured to produce as a representational symbol of validity, the symbol "OK", and said "OK" symbol is defined by said at least one positive control area in combination with another positive control area for a different analyte than said one positive control area, and further wherein said patient sample-analyte area is on another of said reaction surfaces and spaced away from said reaction surface of said two control areas, and wherein said two control areas occupy only the approximate center portion of the reaction surface containing them so that they occupy less than the total area of said reaction surface containing them, so that false positives are readily distinguished by the user.

16. A device as defined in claim 15, wherein another of said two control areas of said reaction surface is effective, if activated to produce a visual indication, to negate said "OK" symbol.

17. A device as defined in claim 16, wherein said another area is said negative control area.

18. In a solid phase assay device for use in a binding assay to determine the presence of an analyte in a liquid sample, the device comprising a plurality of reaction surfaces while comprise at least one of positive control area, a negative control area and a patient sample-analyte area, wherein at least one of said reaction surfaces have at least two of said areas taken from any two of said positive control, said negative control and said patient sample analyte combined and configured together so that said two areas produce, in the presence of an appropriate analyte, a representational symbol selected from words and pictures that area of a predetermined, connected shape and are informative of the test result, the improvement wherein said at least two areas configured together are the positive and negative controls on one of said reaction surfaces and said symbol is formed so as to be indicative of either of two exclusive alternatives: that the test device and procedure are operating satisfactorily, or they are not operating satisfactorily, and wherein said negative control area comprises an antibody specific to the analyte being tested.

19. In a solid phase assay device for use in a binding assay to determine the presence of multiple analytes in a liquid sample, the device comprising at least one reaction surface having at least one positive control area, a negative control area and a patient sample-analyte area, at least one of said areas being configured to produce, in the presence of an appropriate analyte, a predetermined, connected symbol representing the actual results of the test;

the improvement wherein said at least one area is configured to produce the representational symbol "OK", and said "OK" symbol is defined by said at least one positive control area in combination with another positive control area for a different analyte than said one positive control area, and wherein said negative control area comprises an antibody specific to the analyte being tested.

* * * * *

UNITED STATES PATENT AND TRADEMARK OFFICE
CERTIFICATE OF CORRECTION

PATENT NO. : 5,132,085
DATED : July 21, 1992
INVENTOR(S) : Geraldine A. Pelanek

It is certified that error appears in the above-identified patent and that said Letters Patent is hereby corrected as shown below:

Column 1, line 62 should read: --the negative control, which is not used with the "+" or--.

Column 1, line 65 should read: --denatured. The negative control areas for the aforeasaid EPA 217,403 and its U.S. counter- --.

Column 3, line 64 should read: --4,921,677, the details of which are hereby expressly incor- --.

Signed and Sealed this

Fifth Day of October, 1993

Attest:

BRUCE LEHMAN

*Attesting Officer*   *Commissioner of Patents and Trademarks*